United States Patent [19]

Stefan

[11] Patent Number: 4,962,757
[45] Date of Patent: Oct. 16, 1990

[54] SUTURE LOOP FOR CATHETERS

[75] Inventor: Michael S. Stefan, Costa Mesa, Calif.

[73] Assignee: Baxter International Inc., Deerfield, Ill.

[21] Appl. No.: 316,613

[22] Filed: Feb. 28, 1989

[51] Int. Cl.5 .......................................... A61M 39/00
[52] U.S. Cl. ........................... 128/DIG. 26; 604/174; 604/177; 604/180; D24/128
[58] Field of Search ................... D24/51, 54; 128/DIG. 26; 604/174–180

[56] References Cited

U.S. PATENT DOCUMENTS

| | | | |
|---|---|---|---|
| D. 289,689 | 5/1987 | Decsi et al. | D24/54 |
| 3,046,984 | 7/1962 | Eby | 604/180 |
| 3,046,989 | 7/1962 | Hill | 604/180 |
| 3,430,300 | 3/1969 | Doan | 24/304 |
| 3,574,306 | 4/1971 | Alden | 604/162 |
| 3,630,195 | 12/1971 | Santomieri | 604/180 |
| 3,677,250 | 7/1972 | Thomas | 604/180 |
| 3,696,920 | 10/1972 | Lahay | 604/180 |
| 3,702,612 | 11/1972 | Schlesinger | 604/180 |
| 3,826,254 | 7/1974 | Mellor | 604/180 |
| 3,834,380 | 9/1974 | Boyd | 604/180 |
| 3,918,446 | 11/1975 | Buttaravoli | 604/180 |
| 3,973,565 | 8/1976 | Steer | 604/180 |
| 4,059,105 | 11/1977 | Cutruzzula | 604/180 |
| 4,074,397 | 2/1978 | Rosin | 24/304 |
| 4,122,857 | 10/1978 | Haerr | 604/180 |
| 4,142,527 | 3/1979 | Garcia | 604/180 |
| 4,165,748 | 8/1979 | Johnson | 604/180 |
| 4,333,468 | 6/1982 | Geist | 128/DIG. 26 |
| 4,336,806 | 6/1982 | Eldridge, Jr. | 128/DIG. 26 |
| 4,392,853 | 7/1983 | Muto | 604/180 |
| 4,583,976 | 4/1986 | Ferguson | 128/DIG. 26 |
| 4,617,017 | 10/1986 | Hubbard et al. | 604/179 |
| 4,726,716 | 2/1988 | McGuire | 128/DIG. 26 |

Primary Examiner—Randall L. Green
Assistant Examiner—Gary Jackson
Attorney, Agent, or Firm—Debra Dahl Condino

[57] ABSTRACT

The present invention provides a device for securing a catheter or other tubing to a patient by means of suturing. The device comprises an adhesive backed strip having a first portion and a second portion defined by a fold line centered between the first and second portion along a transverse axis of the strip. Preferably, each portion has two holes formed therein with a channel provided between the holes along an axis parallel to the fold line. Thus, when the strip is folded along the fold line over a catheter or tubing, the channel of the first portion overlies the channel of the second portion forming a single channel within which the catheter or tubing is positioned, and the holes of the first portion overlie the holes of the second portion providing a hole on each side of the catheter or tubing to serve as a suture site.

8 Claims, 5 Drawing Sheets

SUTURE LOOP FOR CATHETERS

FIELD OF INVENTION

The present invention relates to a suture loop which, if deemed necessary by the physician, can be used to secure a catheter or other tubing to a patient by means of suturing.

BACKGROUND OF THE INVENTION

In the medical field, it is often desirable to utilize a drug infusion catheter to deliver several IV fluids to a patient at one time. The fluids may include a parenteral fluid and one or more medications. In such a case, a drug infusion catheter with two or more delivery lumens may be used. A typical drug infusion catheter is shown in FIG. 1.

When a drug infusion catheter is used, it is often left in the patient's vascular system for extended periods of time, sometimes as long as 48 hours. In order to secure the catheter in place, the physician often sutures the catheter to the patient at or near the insertion site. This prevents the catheter from pulling out or advancing further into the patient's vascular system. This in turn prevents contamination of the patient, which can occur if the catheter portion that has been outside the body and exposed to the environment slips into the patient's vessel.

In addition to drug infusion catheters, other types of catheters for other medical applications may also need to be sutured to the patient at or near the insertion site.

Figure 1:
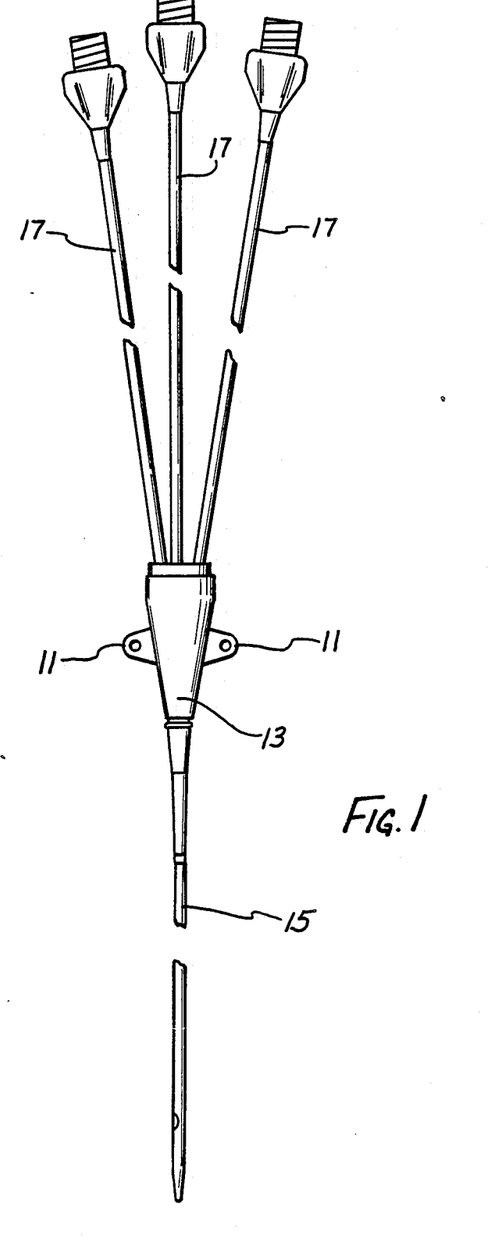
FIG. 1 is a drug-infusion catheter having suture loops integral with the backform.

As shown in FIG. 1, suture loops are generally provided on the backform 13 of a catheter, that is, the connector between the catheter 15 and the extension tubes 17 which communicate with the lumens in the catheter. Typically, the backform 13 is injection molded with a suture loop 11 on either side as shown in FIG. 1. Thus, the suture loops 11 are integral with the backform 13 of the drug infusion catheter 15.

Figure 2:
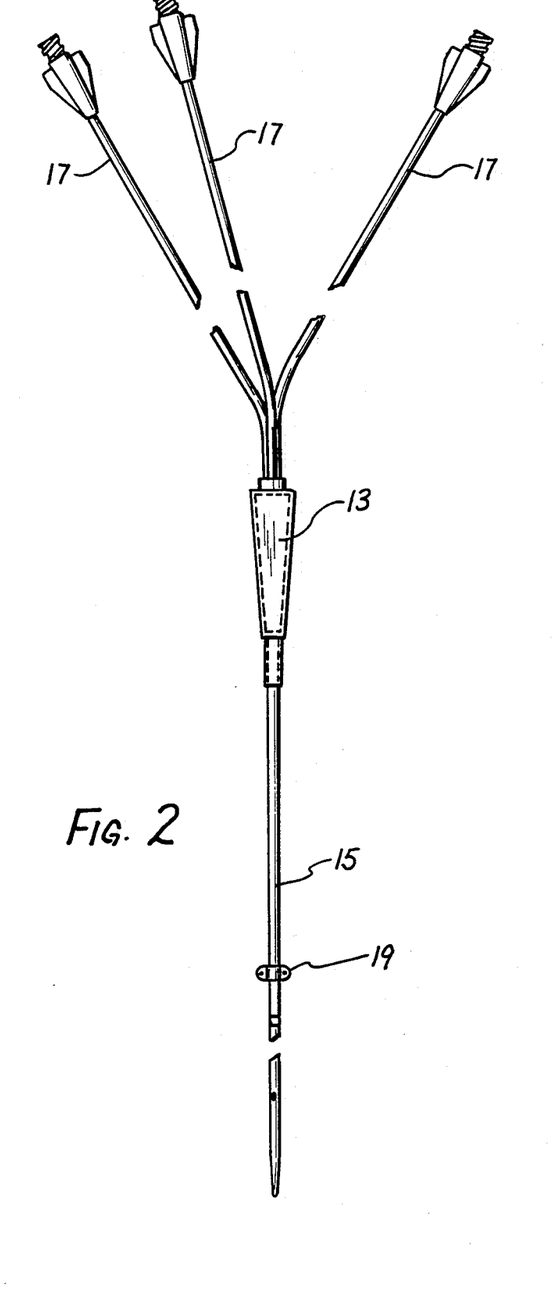
FIG. 2 is a drug-infusion catheter with a suture loop adhesively-bonded to the catheter tubing.

The disadvantage of this type of suture loop is that if the catheter is not inserted completely into the patient's vascular system, the suture loops 11 may be positioned too distant from the insertion site to provide proper catheter anchoring. Attempts to solve this problem have resulted in a suture loop permanently positioned along the catheter tube slightly distal of the backform as shown in FIG. 2.

The suture loop 19 is typically a separate injection-molded part formed of polyvinyl chloride that is adhesively-bonded directly to the catheter 15 at the desired location during manufacture. This practice limits the suture loop's utility to those cases where the catheter is inserted to some predetermined depth. Unless the catheter is advanced to the predetermined depth, the suture loop will not be positioned at the desired location for properly anchoring the catheter. Adhesively-bonding the suture loop to the catheter has the additional disadvantage of creating a stress-concentration and reducing the load-carrying capability of the catheter body tubing. This type of suture loop also has an added cost of the labor involved in permanently attaching the suture loop to the catheter during manufacture.

Figures 3, 4:
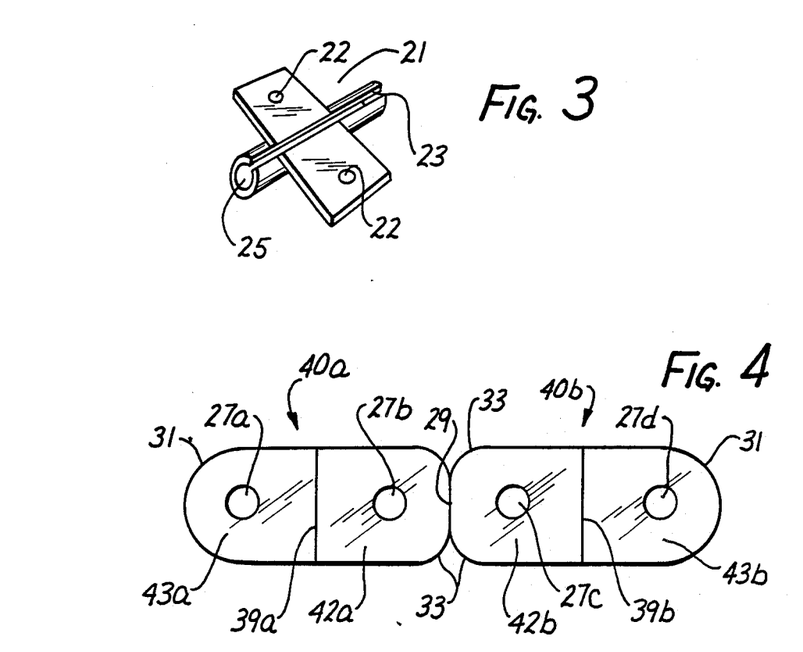
FIG. 3 is an injection-molded slip-on suture loop with a pre-formed slot.
FIG. 4 is a bottom view of a preferred embodiment of the suture loop of the present invention in its fully extended position.

Attempts have been made to create a suture loop that can be positioned anywhere along the length of the catheter, such as the suture loop 21 shown in FIG. 3. This type of suture loop is injection-molded with suture loop holes 22 and a pre-formed slot 23 which permits the suture loop to be slipped onto a catheter at any position along the length of the catheter tubing. The suture loop is typically formed of a pliable elastomeric material so that the slot can be opened to receive the catheter but yet is resilient enough to partially close onto the catheter.

Other suture loops have been provided similar to that shown in FIG. 3 but without the pre-formed slot so that the suture loop is slid onto the catheter over the catheter tip and slid to the desired location along the length of the catheter tubing prior to insertion of the catheter into the patient. The disadvantage of these two suture loops is that fluids from the patient's body, medical cleansing agents, medications and/or other liquids the patient might be treated with tend to wet the surface of the catheter, causing fluid to enter the channel 25 formed within the suture loop. This can cause the suture loop to slip along the catheter tubing resulting in unstable anchorage of the catheter.

OBJECTS AND SUMMARY OF THE INVENTION

It is therefore an object of the present invention to provide a suture loop that can be placed anywhere along the length of the catheter tubing by the physician.

Another object of the present invention is to provide a suture loop that would minimize and would not be affected by accumulation of fluids within the channel surrounding the catheter tubing, thereby preventing the problems associated with slippage of the suture loop.

The present invention in general provides a device for securing a catheter or other tubing to a patient by means of suturing. The device comprises an adhesive-backed strip with holes formed therein so that when the strip is folded over the catheter or tubing with adhesive sides together, at least one hole is provided through which the catheter can be sutured to the patient.

In one preferred embodiment, the adhesive-backed strip has a first portion and a second portion separated by a fold line. The fold line is preferably centered between the first and second portion along a transverse axis of the strip. Preferably, each portion has two holes formed therein with a channel provided between the holes along an axis parallel to the fold line. Thus, when the strip is folded along the fold line over a catheter or tubing, the channel of the first portion overlies the channel of the second portion forming a single channel within which the catheter or tubing is positioned, and the holes of the first portion overlie the holes of the second portion providing a hole on each side of the catheter or tubing to serve as a suture site.

Preferably, the adhesive-backed strip is made of a polymeric material, such as a closed cell polyethylene foam, with adhesive coating on one side and a pliant backing, preferably a plastic film adhesively attached to the other side. The channels are then provided by forming a slit in the polymeric material that does not penetrate the pliant backing. The adhesive-backed strip could also be fabric or some other soft, pliable substance.

For shipping and handling, the suture loop is preferably applied to an oversized adhesive release liner so that the suture loop can easily be grasped and removed when needed. Preferably, the suture loop is mounted on the adhesive release liner in a T-formation wherein the inner ends of the first and second portions, which are adjacent to the fold line, are folded with adhesive sides together, and the outer ends of each portion are applied to the adhesive release liner. The adhesively joined inner ends provide a handle for the physician to grasp to quickly remove the suture loop from the release liner and to manipulate the suture loop to the desired position on the catheter or tubing prior to attaching it to the catheter.

In the preferred embodiment, the channels provided in each portion of the adhesive-backed strip define the inner ends and the outer ends and facilitate the manipulation of the adhesive strip into the T-configuration. When the inner ends are adhesively joined and the outer ends are applied to the adhesive release liner, the channels form a crotch between the outer ends. The crotch serves as an indexing means for engagement with the catheter or tubing when the adhesive-backed strip is removed from the release liner.

DETAILED DESCRIPTION OF THE PREFERRED EMBODIMENT

Referring to FIG. 4, a preferred embodiment of the suture loop of the present invention is shown in its fully-extended position. The suture loop is an adhesive-backed strip with four holes 27 a, b, c and d formed therein. A fold line 29 is provided in the center of the strip to assist in folding the strip over a catheter or other tubing. The holes 27a, b, c and are positioned along the adhesive strip on either side of the fold line 29 so that when the adhesive strip is folded onto itself, holes 27a and d correspond to each other and holes 27b and c correspond to each other. The adhesive-backed strip is folded onto itself over a catheter so that the catheter is positioned between the pair of holes so formed.

In the preferred embodiment, four holes are provided in the strip so that when the strip is folded over, one hole is provided on either side of the catheter. However, in another embodiment two holes may be provided in the strip so that when the strip is folded over the catheter, only one hole is provided for suturing the catheter to the patient. Alternatively, more than four holes could be provided so that when the strip is folded over a catheter three, four or any number of suture holes are provided. The number of holes provided is not critical to the invention, although two holes, one on either side of the catheter is preferred for stable anchoring.

Preferably, the adhesive strip shown in FIG. 4 has rounded outer edges 31 and rounded inner edges 33 formed adjacent to the fold line 29. The rounded edges are a preferred choice, but outer edges 31 could be squared with no rounding of inner edges 33, thereby forming an elongated rectangular strip which would function in the same way as the strip shown in FIG. 4.

Figure 5:
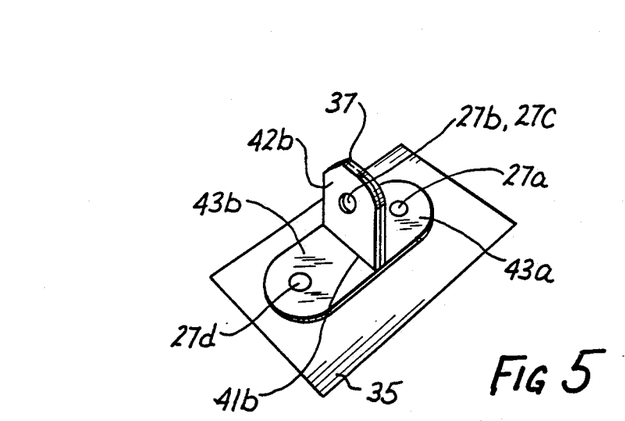
FIG. 5 is a preferred embodiment of the suture loop of the present invention in a T-configuration mounted on an adhesive release liner.

Referring to FIG. 5, a preferred means of mounting the adhesive strip of FIG. 4 on adhesive release paper for shipping and handling by the physician is shown. Preferably, one-half of the adhesive strip is folded onto itself and the other half provides outer ends which are splayed apart and mounted on adhesive-release liner 35. The suture loop mounted on the release liner in this way forms the general shape of a "T". The T-configuration provides handle 37 which the physician can easily grasp to remove the suture loop from the release liner 35 and which can be used to manipulate the suture loop to the desired position along the length of the catheter tubing prior to joining the outer ends to each other.

Although the T-configuration is the preferred configuration, the suture loop could be provided on release liner in its fully extended position as shown in FIG. 4 and simply peeled off by the physician prior to folding it over a catheter.

Referring to FIG. 4, the T-configuration is more easily achieved by providing channel 39a in the first portion 40a of the adhesive strip and channel 39b in the second portion 40b of the adhesive strip. Channel 39a is positioned between holes 27a and 27b, parallel to fold line 29. Channel 39b is positioned between holes 27c and 27d, also parallel to fold line 29. Channels 39a and 39b overlie each other when the adhesive strip is folded over the catheter tubing thereby creating a single channel through which the catheter tubing passes. The channel serves as a catheter indexing means for positioning and placement of the suture loop around the catheter tubing. Channels 39a and 39b also facilitate bending the strip along lines 41a and 41b shown in FIG. 7 when inner edges 42a and b are folded together and outer edges 43a and b are splayed apart to form the T- configuration.

Figure 7:
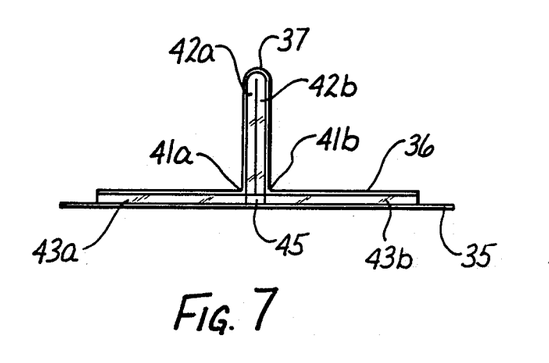
FIG. 7 is a side view of the suture loop shown in FIG. 5.

A preferred material for the adhesive-backed strip is a laminate of polymeric foam tape coated on both sides with an agressive high shear adhesive system and a pliant backing applied to one side of the foam tape. The laminate construction is best shown in FIG. 7. The pliant backing 36 is preferably a plastic film, such as a polyolefin, and the foam tape is preferably a closed-cell polyethylene, both of which are commercially available. A plastic film such as polyolefin is preferred because it is very strong and tear-resistant, yet pliable and soft to the touch.

The foam tape is preferred because it has sufficient thickness and softness to grip the catheter without deforming the catheter but yet is resilient enough to provide a tight closure around the catheter which together with the adhesive bonding to the catheter minimizes accumulation of undesired fluids in the channel surrounding the catheter. This in turn prevents slippage of the catheter once it has been positioned by the physician at the desired location along the catheter tubing. In the event there is some minimal fluid accumulation, the adhesive bonding also minimizes the slippage effect that fluid accumulation would otherwise have.

Figure 8:
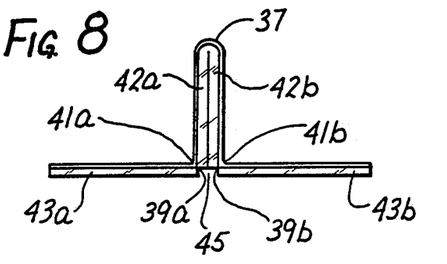
FIG. 8 is a side view of the suture loop shown in FIG. 5 after it has been removed from the release liner.

The adhesive bonding to the catheter is facilitated by creating channels 39a and 39b in the foam tape. As shown in FIG. 8, these channels are preferably formed by slitting or cutting through the foam tape at 39a and 39b but not cutting through the pliant backing, thus when inner edges 42a and 42b are folded together, the outer edges 43a and 43b swing outwardly to form a crotch 45.

The crotch allows for positive placement of the suture loop on the catheter tubing by positioning the crotch over the tubing at the desired location and then folding outer edges 43a and 43b together to seal the suture loop around the catheter tubing. The preformed channels 39a and 39b create a single channel when the suture loop is closed around the catheter tubing and provide for a tighter fit around the catheter. The air space in the channel around the catheter will be proportional to the bond strength of the adhesive on the strip. The channel may not be necessary if the adhesive on the strip is strong and will not separate due to the resiliency of the catheter tube and if the strip material is of sufficient thickness and softness to conform around the catheter tubing.

In another preferred embodiment, adhesive coating on the foam tape is also provided within the precut channels of the foam tape so that when crotch 45 is positioned against the catheter tubing and outer edges 43a and 43b are folded together, all four edges of channels 39a and 39b grip the catheter.

Figure 6:
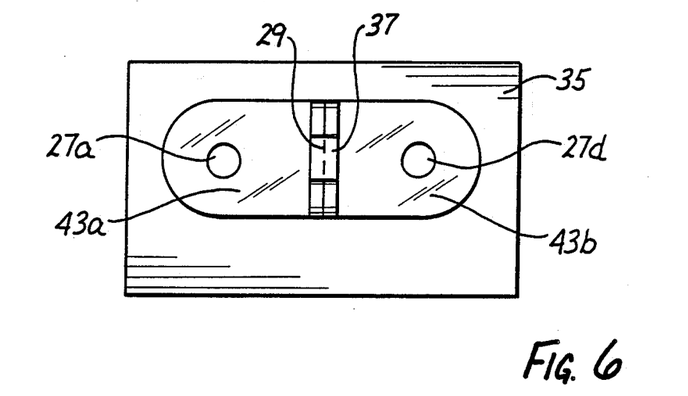
FIG. 6 is a top view of the suture loop shown in FIG. 5.

Referring to FIG. 6, there is shown a top plan view of the T-configuration. The rounded edges 33 on the preassembled adhesively joined inner edges 42a and 42b are separated by fold line 29 which is preferably a perforated line provided in pliant backing 36. The perforation aids in folding the adhesive backed strip along fold line 29. In addition, or in the alternative, a slit can be provided in the foam tape or other material used for the strip at the fold line to further aid in folding the strip along the fold line. Like channels 39a and 39b the slit at the fold line would not be deep enough to penetrate the pliant backing.

Because of rounded edges 33, the length of fold line 29 is less than the length of channels 39a and b. In another embodiment, rounded edges 33 would not be provided and fold line 29 would be the same length as precut channels 39a and 39b. The width of the adhesive strip would thus be uniform along its length.

The flat pattern of the adhesive strip shown in FIG. 4 or in another embodiment, an elongated rectangular strip with squared edges, can be easily mass produced by die cutting from a roll of the material used for the adhesive backed strip. Accordingly, the suture loop of the present invention presents tremendous cost savings over prior art suture loops which are typically injection-molded plastic parts.

To use the suture loop of the present invention, the physician first inserts the catheter into the patient to the proper depth, then grasps the suture loop at its preassembled end (the adhesively joined inner ends 42a and 42b), and pulls the suture loop off the release liner to expose the adhesive. He then places the catheter in crotch 45 of the suture loop, and with thumb and forefinger, brings the exposed adhesive tape around the catheter body and finally upon itself. He can then pass sutures through the openings or holes in the suture loop to secure it to the patient.

Figure 9:
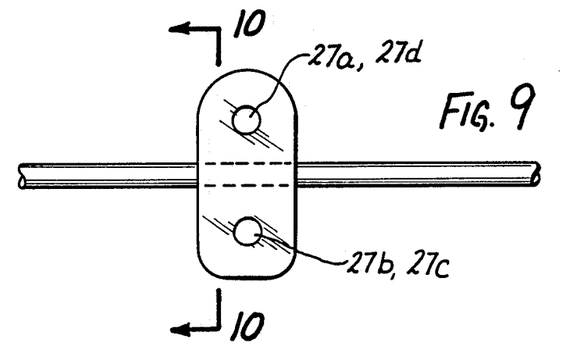
FIG. 9 is a top view of the suture loop of the present invention after it has been attached to a catheter.
Figure 10:
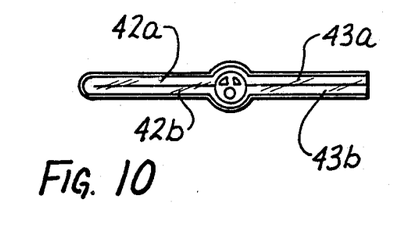
FIG. 10 is a cross-sectional view of the suture loop of the present invention taken along line 10—10 of FIG. 9.

Referring to FIGS. 9 and 10, the suture loop of the present application is shown attached to a drug infusion catheter. FIG. 9 is a top view and FIG. 10 is a cross-sectional view taken along line 10—10 of FIG. 9.

When the suture loop is attached to the catheter, its total thickness is preferably less than the minimum diameter of the catheter tubing. The foam tape is preferably 1/32 inch thick, the pliant backing of polyolefin is preferably 5 mil thick, and the acrylic coating is preferably ½ mil thick. Any other dimensions are suitable for the suture loop of the present invention.

The release liner paper is commercially available and is typically silicone treated paper. The release liner is preferably oversized so that when the physician grasps the preassembled end, he can also grasp a corner of the liner and peel it off to expose the adhesive of the suture loop. The oversizing of release liner 35 is The foam tape with adhesive coating embodiment of the present invention is advantageous because it firmly adheres to the catheter body and distributes the restraining forces without creating any significant stress concentration effect. The conventional method of adhesive bonding of an injection molded suture loop to the catheter, as shown in FIG. 2, tends to create a stress concentration and reduces the load-carrying capability of the catheter body tubing.

The adhesive-backed strip also provides the advantage of reducing the cost of labor involved in creating a separate molded part and adhesively bonding it to the catheter during manufacture. The present invention shifts the labor of locating the suture loop to the physician, thus providing an immediate cost savings. The additional advantage of the suture loop of the present invention is that by shifting the labor to the physician, the suture loop can be placed precisely at the desired location.

The invention described may be embodied in other specific forms without departing from its spirit or essential characteristics. The described embodiments are to be considered in all respects only as illustrative and not restrictive. The scope of the invention is therefore indicated by the appended claim, rather than by the foregoing description. All changes which come within the meaning and range of the equivalency of the claims are to be embraced within their scope.

What is claimed is:

1. A device for securing tubing to a patient by means of suturing, comprising:
    an elongated strip having two ends and two sides with adhesive applied to one side, said strip having a first portion and a second portion, each portion having at least one hole formed therein and a channel formed on the adhesive side of the strip so that when the adhesive side of the strip is folded over the tubing and the ends are pressed together, the channels overlie each other forming a single channel within the adhesively joined strip to secure the tubing in place, and the holes overlie each other to provide a suture site.

2. A device according to claim 1, wherein each portion has two holes formed therein, one on each side of the channel, so that when the strip is folded over the tubing, the holes in the first portion overlie the holes in the second portion providing a hole on each side of the tubing to serve as suture sites.

3. A device according to claim 1 or 2, wherein the adhesive side of the strip is applied to an adhesive release liner and removed from said liner when needed for suturing.

4. A device according to claim 1 or 2, wherein the strip comprises foam tape with adhesive coating on one side and a pliant backing adhesively attached to the other side.

5. A device according to claim 1 or 2, wherein the strip comprises foam tape with adhesive coating on one side and a pliant backing adhesively attached to the other side and the channel provided in each portion of the adhesive strip is formed by a slit which penetrates the adhesive side of the foam tape but leaves the pliant backing intact.

6. A device according to claim 1 or 2, wherein the first and second portions are separated by a fold line provided along a transverse axis of the strip and each portion has inner and outer ends defined by the channel formed in each portion, the inner ends are adjacent the fold line, so that when the strip is folded along the fold line the inner ends of each portion can be adhesively joined and the outer ends of each portion can be applied to the adhesive release liner, the channels provided in each portion thereby forming a crotch between the outer ends of each portion for engagement with the tubing when the outer ends are removed from the release liner.

7. A device according to claim 6, wherein the adhesively joined inner ends of each portion provide means for grasping the strip for quick release from the release liner and for handling the strip and attaching it to the tubing.

8. A device according to claim 1 or 2, wherein said channel in each portion of the strip is a slit formed in the adhesive side of each portion that does not penetrate the strip completely.

* * * * *

UNITED STATES PATENT AND TRADEMARK OFFICE
CERTIFICATE OF CORRECTION

PATENT NO. : 4,962,757
DATED : October 16, 1990
INVENTOR(S) : Michael S. Stefan

It is certified that error appears in the above-identified patent and that said Letters Patent is hereby corrected as shown below:

Column 6, line 15, after "....35 is", insert --shown in Fig. 7.--

Signed and Sealed this

Seventh Day of April, 1992

Attest:

HARRY F. MANBECK, JR.

*Attesting Officer*  *Commissioner of Patents and Trademarks*